United States Patent [19]

Owades

[11] 4,170,638
[45] Oct. 9, 1979

[54] METHOD FOR PRODUCING A DEODORANT

[75] Inventor: Joseph L. Owades, Boston, Mass.

[73] Assignee: S. S. Steiner, Inc., New York, N.Y.

[21] Appl. No.: 904,775

[22] Filed: May 11, 1978

Related U.S. Application Data

[63] Continuation of Ser. No. 739,305, Nov. 5, 1976, abandoned.

[51] Int. Cl.$^2$ .............................................. A61K 7/32
[52] U.S. Cl. .................................... 424/65; 252/107; 424/DIG. 5; 424/47; 424/76
[58] Field of Search ..................... 424/65, DIG. 5, 76, 424/47; 252/107

[56] References Cited

FOREIGN PATENT DOCUMENTS 745607  2/1956  United Kingdom ..................... 424/230

OTHER PUBLICATIONS

Stecker, Soc. of Cosm. Chemists Journal, 1960, vol. 11, pp. 347 to 362.
Chem. Abs., 1949, vol. 43, pp. 5444 to 5445.
Chem. Abs., 1964, vol. 60, p. 7142.
Chem. Abs., 1967, vol. 66, p. 22108f.
Chem. Abs., 1965, vol. 62, p. 11626.
Chem. Abs., 1973, p. 140348e, vol. 78.
Chem. Abs., 1973, vol. 78, pp. 56705m, 62061q.
Ford et al., Chem. Abs., vol. 18, p. 3448, 1924.

Primary Examiner—Dale R. Ore
Attorney, Agent, or Firm—Strimbeck & Soloway

[57] ABSTRACT

There are provided new deodorant compositions which are suitable for application to human skin, the compositions comprising an extract of hops as an active antibody odor ingredient which is present in an amount at least sufficient to provide bacteriostatic activity.

11 Claims, No Drawings

METHOD FOR PRODUCING A DEODORANT

This application is a continuation of my copending application Ser. No. 739,305, filed Nov. 5, 1976 for Hop Compositions as Bacteriostatic Agents for Deodorants is now abandoned.

This invention relates to novel deodorant preparations such as liquid or solid deodorant soaps, lotions, aerosol sprays, sticks, creams, powders, oils and the like, which include as a bacteriostatic agent which inhibits the growth of odor-causing skin bacteria, e.g., gram-positive bacteria, an organic solvent soluble hop extract.

BACKGROUND OF THE INVENTION

Prior art studies of the human skin have shown that epidermal tissue supports a relatively large population of microorganisms, which predominantly comprise bacteria. Skin bacteria are divided into essentially two categories: (1) transient bacteria, which come and go during the course of ordinary day-to-day contact of human skin with its environment, and (2) resident bacteria, which thrive on human skin over an indefinite period of time.

While transient bacteria are readily removed by normal washing with ordinary soap, resident bacteria are more difficult to remove because they are more deeply embedded in the skin. Resident bacteria can be classified into two types, gram-positive and gram-negative, according to their reaction to the well-known Gram staining method. It is known that when gram-positive bacteria come into contact with the axillary secretions of apocrine sweat, which are normally sterile and odorless, gram-positive bacteria cause these secretions to become malodorous, thus producing the typical acrid body odor. In contrast to gram-positive types of bacteria, gram-negative bacteria are not a cause of body odor. However, over 99% of resident bacteria are of the odor-causing gram-positive variety.

Thus, the prevention or amelioration of human body odor can be brought about by reducing the number of resident gram-positive bacteria in or on the skin. This can be accomplished by regular washings with deodorant soaps and/or the application of other deodorant preparations such as aerosol spray deodorants, sticks, creams, etc., which contain active antibacterial ingredients.

It has now been discovered that when hops, i.e., the flower of the humulus lupulus plant, is extracted with an organic solvent and the solvent is removed, a residue, or extract, is obtained which acts as an effective bacteriostatic agent in soaps and other cosmetic preparations for application to human skin and which prevents or ameliorates body odor. It has been found, for example, that soap solutions containing only relatively minor amounts, e.g., about 1% by weight, of the hop extract, effectively inhibit the growth of odor-causing skin bacteria such as *Staphylococcus aureus* and *Staphylococcus epidermis*.

The antibacterial activity of hop extract in the presence of soaps and other preparations for human skin has not been previously known. Although certain constituents of hops have been known to exert antibacterial activity against the very fastidious microorganisms that exist in beer, it is unexpected that hop constituents can act as effective antibacterial ingredients in soaps and other cosmetic compositions, which have often been found to neutralize or destroy the microbicidal or bacteriostatic power of antiseptic compounds. The hop extract of this invention possesses a number of other properties, in addition to bacteriostatic activity, which make it suitable for use in deodorant preparations. It is surprisingly compatible with other ingredients employed in deodorant preparations, substantive to human skin, i.e., sticks to human skin, soluble in soaps and oils, nontoxic to animal life and non-irritating to human skin.

DESCRIPTION OF THE INVENTION

Accordingly, the present invention provides, in its broadest aspects, a deodorant composition which is suitable for application to human skin, the composition comprising as an active odor preventing or ameliorating ingredient, an extract of hops in an amount at least sufficient to provide antibacterial activity.

The bacteriostatic extract may be obtained by contacting the flower of the humulus lupulus plant with an organic solvent, using conventional procedures of extraction. Specific conditions for carrying out the extraction will, of course, vary, depending on the circumstances. Preferably, however, the hops are immersed in, or otherwise contacted with, an organic solvent at atmospheric pressure and ambient temperature, for a period of time ranging from about ½ to about 4 hours. After contacting the hops, the organic solvent is removed and a substantially solvent free residue is obtained. The residue is a greenish viscous liquid, almost solid at room temperature, having a pleasant sweet aroma.

This residue, or extract, is remarkably effective in inhibiting the growth of odor-causing skin bacteria, such as gram-positive bacteria. The exact chemical composition of the extract is very complex, but it is known to contain a series of humulones and lupulones. However, the humulone fraction can be removed, e.g., by precipitation as a metallic salt, for instance, as a salt of lead or calcium and the extract will still retain its bacteriostatic effectiveness.

A broad variety of organic solvents can be used to carry out the extraction. Preferably, however, the solvent is selected from among alkanes, especially alkanes of from 5 to 12 carbon atoms, such as pentane, hexane, heptane, octane, nonane, decane, dodecane, and the like; alcohols, such as methanol, ethanol, propanol, butanol, pentanol, hexanol, octanol, nonanol, decanol, and the like; chlorinated hydrocarbons, such as methyl chloride, methylene chloride, and the like; petroleum ether; and aromatic hydrocarbons, such as benzene, toluene, xylene, naphtha, and the like.

The type of carrier medium or vehicle which can be used for the bacteriostatic hop extract can very broadly. Thus, the deodorant compositions of this invention can comprise liquid or solid soaps, creams, pastes, aerosol sprays, powders, sticks, and the like. The method of preparation is not critical, and conventional procedures can be employed. Preferably, the hop extract is included in a soap, which can otherwise be prepared in a conventional manner, i.e., from naturally occurring triglycerides (animal and vegetable fats), by hydrolysis of the ester linkages, e.g., sodium sterate. The addition of the hop extract is preferably made during the crutching operation.

The hop extract of this invention can also be incorporated into creams, pastes, sticks, powders, aerosol sprays and the like. When the deodorant composition is prepared in the form of a paste or cream, for example, the hop extract can be dissolved in a base, or carrier, comprised of an inert organic material, e.g., petroleum jelly, hydrogenated lard, hydrogenated vegetable oil, or the like, or an emulsion of such materials with water. Dry solids such as talc, clay, titanium dioxide, and the like, are then sifted in slowly, with mixing, until the desired consistency is obtained.

By way of illustration, deodorant powders can be prepared by blending the hop extract with a base material, such as talc, corn starch, precipitated chalk, or the like, and sifting the blend. Deodorant sticks can be made, illustratively, by blending soap, emollients, water, alcohol and the hop extract at an elevated temperature, pouring the mixture into a mold of the desired shape, and allowing the blend to cool and harden.

The hop extract of this invention is also suitable for use in deodorant sprays, which are typically prepared from water and alcohol solutions of an antibacterial agent or astringent compound, perfume, preservatives, and the like, and a propellant, e.g., Freon.

Other ingredients such as perfumes, emollients, emulsifying agents, stabilizers, physiologically acceptable coloring agents, and the like, can be added to the deodorant compositions in minor amounts for their conventionally employed purposes.

The amounts for the various ingredients in the deodorant compositions can vary broadly, it being essential only that the bacteriostatic hop extract is added in an amount which is at least sufficient to impart bacteriostatic, i.e., bacterial growth inhibiting, activity. This amount will of course, vary, depending on the composition of the particular deodorant preparation. In general, relatively minor amounts are effective, for example, quantities of as little as 1% by weight or less based on the total weight of the deodorant composition. Preferably, amounts of from about 1 to about 5% by weight of hop extract, based on the weight of the total, are employed.

The deodorant compositions of this invention and their methods of preparation are further illustrated in the following examples, which are not intended to be limiting in any manner.

EXAMPLE 1

Two-hundred pounds of Yakima Cluster hops are contacted with methylene chloride at ambient temperature and atmospheric pressure for one-half hour or longer and the solvent is removed. The residue, a greenish viscous liquid having a sweet aroma, is incorporated into a soap during the crutching process, or other suitable stage of the soap-making operation, so that the final soap product contains 2% by weight of hop extract. A deodorant soap according to the present invention is thus obtained.

EXAMPLE 2

Two-hundred pounds of Oregon Cascade hops are extracted with hexane an ambient temperature and atmospheric pressure for one-half hour or longer. The extract is incorporated into a deodorant stick, having a composition as follows:

| Components | % By Weight |
| --- | --- |
| Sodium stearate | 8 |
| Sorbitol | 5 |
| Water | 8 |
| Ethyl alcohol, SDA 40 | 75 |
| Hop extract | 1 |
| Perfume | 3 |

The above composition is prepared by dissolving the hop extract in the alcohol with heat, adding sorbitol and soap with continued heating until the soap dissolves, and then adding perfume. The resulting mixture is poured into a mold and allowed to cool and harden.

EXAMPLE 3

Using the procedure described in Example 1, two-hundred pounds of Yakima Cluster hops are extracted with methylene chloride and the solvent removed. The residue is treated to remove the major part of the humulones. The fraction low in humulones is incorporated into a soap at about 2% concentration.

Other modifications and variations of the present invention will suggest themselves to those skilled in the art in the light of the above description. It is to be understood, therefore, that changes may be made in the particular embodiments described herein which are within the full intended scope of the invention as defined in the appended claims.

I claim:
1. A method for producing a deodorant composition for applying to human skin to inhibit growth of gram-positive bacteria thereon, said method comprising the steps of:
    contacting the flower of the humulus lupulus plant with an organic solvent under conventional extraction conditions to obtain an extract containing humulones and lupulones, and
    admixing said extract with a carrier therefor, which carrier is selected from the group consisting of a liquid soap, a solid soap, a cream, a paste, an aerosol spray, a powder and a stick.
2. A method as defined in claim 1 wherein said organic solvent is selected from the group consisting of an alkane, an alcohol, a chlorinated hydrocarbon, petroleum ether, a mineral oil, a vegetable oil, and an aromatic hydrocarbon.
3. A method as defined in claim 2 wherein said organic solvent is an alkane of from 5 to 12 carbon atoms.
4. A method as defined in claim 3 wherein said alkane comprises hexane.
5. A method as defined in claim 1 including the step of admixing a perfume in said composition.
6. A method as defined in claim 1 including the step of treating said extract to remove the major portion of the humulones contained therein.
7. A method as defined in claim 1, wherein said extract is admixed with said carrier in an amount of at least about 1% by weight, based on the combined weight of extract and carrier.
8. A method as defined in claim 7 wherein said extract is admixed with said carrier in an amount in the range of from about 1 to about 5% by weight, based on the combined weight of extract and carrier.
9. A method as defined in claim 1 wherein said carrier comprises a solid soap.
10. A method as defined in claim 1 wherein said carrier comprises a deodorant stick.
11. A method as defined in claim 1 including the step of admixing an emolient in said composition.

* * * * *